United States Patent [19]

Russell et al.

[11] 4,399,312

[45] Aug. 16, 1983

[54] CATALYTIC PROCESS

[75] Inventors: Michael J. H. Russell, Reading; Barry A. Murrer, Henley-on-Thames, both of England

[73] Assignee: Johnson Matthey Public Limited Company, London, England

[21] Appl. No.: 297,083

[22] Filed: Aug. 27, 1981

[30] Foreign Application Priority Data

Sep. 4, 1980 [GB] United Kingdom ............... 8028521

[51] Int. Cl.³ ............................................. C07C 45/50
[52] U.S. Cl. .................................... 568/454; 568/909; 568/451; 252/431 P; 260/429 R
[58] Field of Search ..................... 568/454, 451, 909

[56] References Cited

U.S. PATENT DOCUMENTS 3,855,307 12/1974 Rony et al. .......................... 568/454
3,937,742 2/1976 Yoo ...................................... 568/454
3,981,925 9/1976 Schwager et al. .................. 568/454
4,306,085 12/1981 Kim et al. ............................ 568/454

FOREIGN PATENT DOCUMENTS 2627354 12/1976 Fed. Rep. of Germany ....... 568/454

Primary Examiner—Werren B. Lone
Attorney, Agent, or Firm—Cushman, Darby & Cushman

[57] ABSTRACT

A process for the hydroformylation of olefins which facilitates recovery of precious metal catalyst and which proceeds under mild conditions comprises using as catalyst a water-soluble complex of a platinum group metal, the reaction mixture including aqueous and organic phases and an amphiphilic reagent.

17 Claims, 1 Drawing Figure

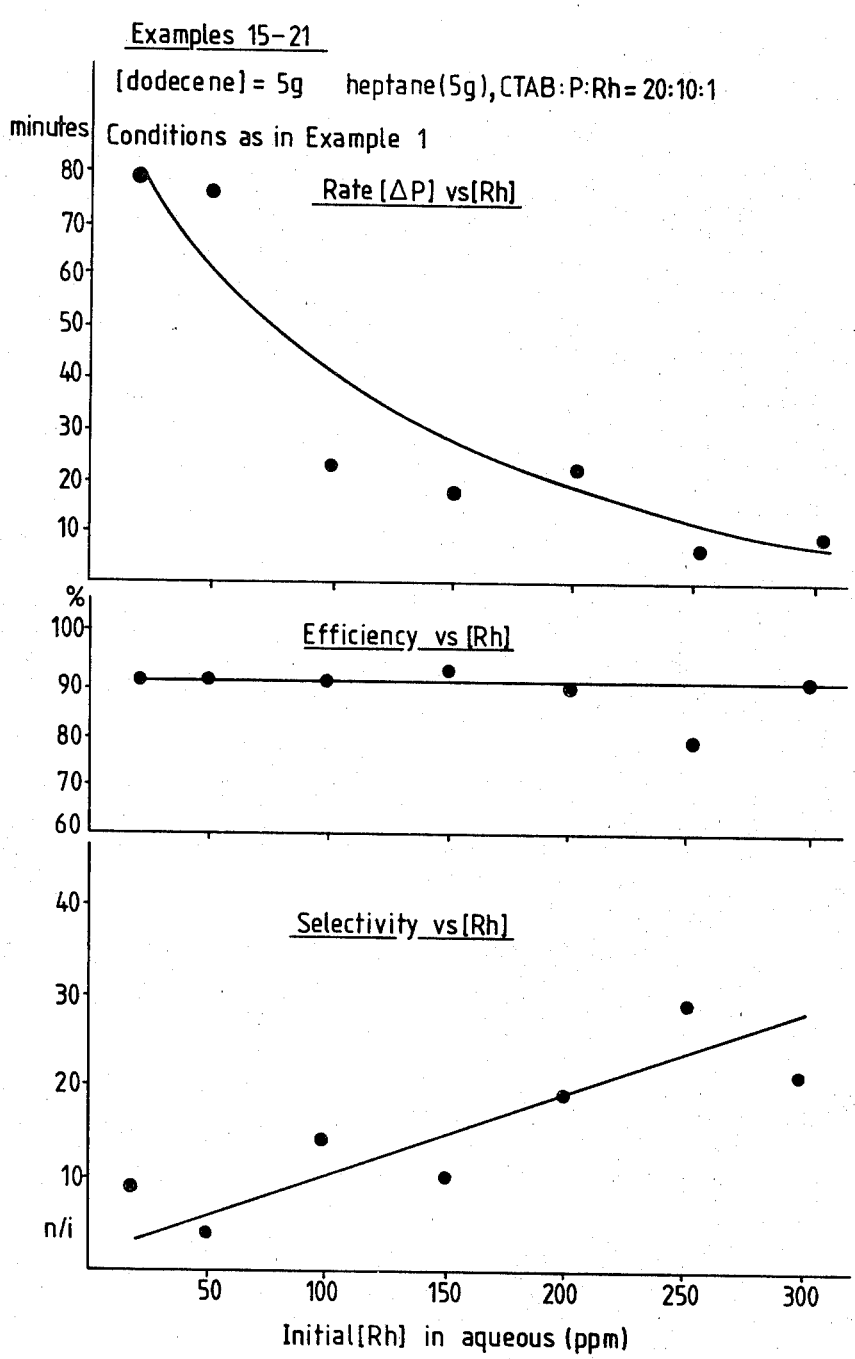

CATALYTIC PROCESS

This invention relates to the hydroformylation of olefins, and provides a two phase catalytic process therefor which operates under mild conditions and in which separation and recovery of catalyst is facilitated.

Hydroformylation of olefins to yield aldehydes and/or alcohols is a well-known and useful industrial process which may use as catalyst a complex of a precious metal such as rhodium and is carried out in the organic phase. The catalyst complex is soluble in the organic phase, with the result that difficulties ensue in separation and recovery of rhodium or other precious metal catalyst.

One proposed solution to this problem is to carry out the reaction in the presence of an aqueous solution of rhodium or a rhodium compound and a sulphonated tri-aryl phosphine, such that the organic phase containing the reaction starting materials and/or products can readily be separated from the aqueous phase containing the catalyst. Such a reaction however requires very high reactor pressures, typically 40 bars (4000 kPa) or greater, and often requires an unacceptably long reaction time. Furthermore, it is difficult to achieve a high n:iso ratio of product aldehydes, which is desirable from the point of view of usefulness in further processes.

We have now found that these disadvantages in the use of a two-phase system may be mitigated or avoided by including in the reaction mixture a reagent which has an affinity for both the organic and aqueous phases. Such reagents may be classified either as phase transfer reagents or as surfactants. For convenience, we refer to such agents generically as "amphiphilic reagents". We have found that these reagents enable the hydroformylation reaction to proceed smoothly under mild conditions and preferably do not interfere with separation and recovery of catalyst from the aqueous phase.

According to the invention, therefore, we provide a catalytic process for the hydroformylation of olefins which comprises reacting together at elevated temperature and pressure an olefin, hydrogen and carbon monoxide in the presence of a catalyst comprising a water-soluble complex of a platinum group metal in a reaction medium comprising an aqueous phase and an organic phase and in the further presence of an amphiphilic reagent.

The organic phase consists essentially of the substrate olefin and/or the hydroformylation reaction product preferably with one or more organic solvents. The substrate olefin may be a terminal or internal olefin having a carbon chain length of $C_3$–$C_{20}$, preferably $C_7$–$C_{14}$. If a solvent is used, it may be selected from common inert aliphatic solvents such as alkanes or aromatic solvents such as toluene or chlorobenzene. We prefer to use $C_5$ to $C_9$ alkanes such as cyclohexane and n-pentane.

The aqueous phase contains the water-soluble complex of platinum group metal. By "platinum group metal" we mean platinum, rhodium, palladium, ruthenium, iridium and osmium. We prefer to use as catalyst a water-soluble complex of rhodium, platinum, ruthenium or palladium, especially rhodium which operates under the mildest conditions. The catalytic complex is preferably formed in situ from a water-soluble precursor compound or complex of platinum group metal and a water-soluble phosphine. The choice of precursor compound or complex is not critical. Examples include [Rh(acac)(CO)$_2$], [RhCl$_3$3H$_2$O], [RhCl(diene)]$_2$, [Rh(diene)$_2$]$^+$A$^-$, [Rh$_2$(C$_5$Me$_5$)$_2$(OH)$_3$]$^+$A$^-$, [Ru$_2$(OH)$_3$(arene)$_2$]$^+$A$^-$, [Pd(allyl)diene]$^+$A$^-$, [Pd$_2$(dba)$_3$], K$_2$[PdCl$_4$], K$_2$[PtCl$_4$], [RuCl$_3$3H$_2$O], Na$_3$[RuCl$_6$] and [Ru$_2$Cl$_4$(arene)$_2$], where acac represents acetylacetonato, a suitable diene is 1,5-cyclooctadiene, suitable arenes include p-cymene (i.e. isopropyltoluene) and hexamethylbenzene, A is a non-complexing anion such as tetraphenylborate or tetrafluoroborate, and dba represents dibenzylidene acetone.

The aqueous phase also contains a water-soluble phosphine which reacts in situ with the catalyst precursor compound or complex and also with hydrogen and/or carbon monoxide to form the catalytic complex. The water-soluble phosphine is preferably a sulfonated or carboxylated triaryl phosphine having the formula

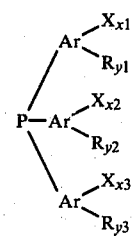

in which the Ar groups are the same or different aryl groups, for example phenyl and naphthyl; the substituent R groups are the same or different and are selected from $C_1$ to $C_4$ linear or branched chain alkyl or alkoxy groups, for example methyl, ethyl, propyl, isopropyl, butyl, methoxy, ethoxy, propoxy or butoxy groups; halogen; hydroxy; nitrile; nitro; amino and $C_1$ to $C_4$ alkyl-substituted amino; the substituent X groups are the same or different and are selected from carboxylic acid, sulphonic acid and salts thereof; $x_1$, $x_2$ and $x_3$ are the same or different integers from 0 to 3 inclusive, provided that at least $x_1$ is equal to or greater than 1; and $y_1$, $y_2$ and $y_3$ are the same or different integers from 0 to 5 inclusive. Preferably Ar is phenyl, X is either COOH or SO$_3$Na, $x_1$ is 1, $x_2$ and $x_3$ are 0 and $y_1$, $y_2$ and $y_3$ are 0. When X is an acid salt, the cation thereof is preferably Na$^+$, although other alkali metal cations such as K$^+$ may alternatively be utilised. Quaternary ammonium cations, for example NH$_4^+$, may also be used.

Preferred water-soluble phosphines include the following compounds:

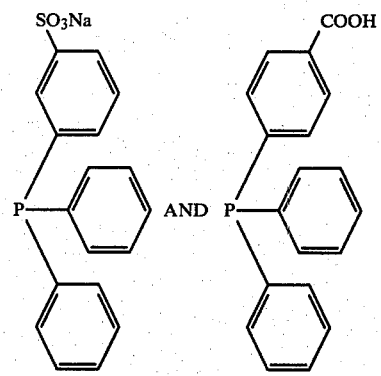

Another example is P(C$_6$H$_4$CO$_2$H)$_3$. Phosphinites of commercially-available polyoxyethylene detergents, for example PPh$_2$(OCH$_2$CH$_2$)$_n$OC$_{12}$H$_{25}$, where n=23, may also be used.

Optionally, the catalyst precursor compound or complex may be reacted in advance with the water-soluble phosphine to form an intermediate precursor compound of the catalytic hydrido/carbonyl-containing complex. Generally speaking, however, it is more convenient to form the catalytic hydrido/carbonyl complex direct from precursor and water-soluble phosphine in situ in the hydroformylation reactor.

The aqueous phase should preferably include free water-soluble phosphines in addition to that required to form the catalytic complex. The free phosphine may be the same as or different from that used to form the catalytic complex although it is preferred to utilise the same phosphine. Conveniently, a stoichiometric excess of the phosphine is added to the reactor both to form the catalytic complex and to provide the free phosphine.

The free phosphine should be present in a mole ratio to precious metal of up to 150:1 although it is generally possible to operate satisfactorily at a ratio of 20:1 or lower, or even 10:1 or lower. The concentration of amphiphilic reagent has an effect on the reaction, however, independently of the phosphine:precious metal ratio.

The ratio of the aqueous to organic phases should be in the range 0.33:1 to 5:1, preferably 0.5:1 to 3:1. Good results have been obtained at ratios of approximately 2:1 and 1:1. Lower ratios of aqueous to organic tend to slow the reaction rate whereas higher ratios tend to cause a greater quantity of precious metal to accumulate in the organic phase.

The concentrations of precious metal in the reaction medium is expressed in terms of parts per million (ppm) of metal based on the aqueous phase. We have found that both the rate of reaction and the selectivity for straight-chain products are increased with increasing precious metal (rhodium) concentration to maxima, after which either a decrease or a tendency to remain the same is observed. Efficiency (that is, percentage conversion to aldehydes) is substantially unaffected by rhodium concentration. Precious metal concentration should be in the range 100 to 500 ppm; preferably 200-400 ppm, a level of 300 ppm being the optimum in many reactions.

The pH of the aqueous phase should preferably be buffered at 7 or greater although there is no intrinsic objection to operating under acid conditions provided that the buffer and the catalyst are compatible and mutually inert.

The purpose of the amphiphilic reagent is to enable the substrate olefin to cross smoothly into the aqueous phase and to enable product aldehyde to cross back to the organic phase. Exceptionally, the amphiphilic reagent may promote inter-phase transfer of catalyst. Desirably, it should contain polar and non-polar moieties to provide the required affinity for both aqueous and organic phases, and should preferably be distributed principally in the aqueous phase with a minor portion in the organic phase. More preferably, the amphiphilic reagent should be substantially soluble in the aqueous and substantially insoluble in the organic, its effectiveness in operation being due, we believe, to its tendency to transport species across the phase boundary in view of the polar and non-polar moieties. An approximate analogy may be drawn between this tendency and the preferred position and orientation of a detergent molecule, at an aqueous/organic phase boundary, generally expressed in terms of "HLB", the hydrophobic-lipophobic balance. Such a quantitative definition is not appropriate as a classification for amphiphilic reagents, however, since the necessary determinations cannot, at least for the most effective ones, be made. The amphiphilic reagent may be anionic, cationic or neutral. Many suitable reagents are available commercially as phase transfer reagents or surfactants. An example of a suitable anionic reagent is sodium dodecyl sulphate; a neutral reagent is commercially available "Brij 35" (ie $[C_{12}H_{25}(OCH_2CH_2)_{23}OH]$) and a cationic reagent is a tetra-alkyl ammonium salt such as cetyltrimethylammonium bromide. Also useful as examples of cationic reagents are other complex ammonium salts such as cetylpyridinium bromide, lauryl and myristyl ammonium bromides and cetyltrimethylammonium acetate. Generally, we prefer to use cationic reagents, or neutral reagents such as polyoxyethylenes, such as "Brij 35". The concentration of amphiphilic reagent relative to precious metal should be up to 100:1 on a molar basis, preferably from 1:1 to 25:1, for example 5:1 or 20:1. We have found in general that increasing quantities of amphiphilic reagent reduce the loss of precious metal to the organic phase.

The reaction conditions of temperatures and pressure are mild. The temperature should be in the range 40°–150° C. Below about 40° C., the rate of reaction is unacceptable slow whereas catalyst deactivation tends to occur at temperatures in excess of 150° C. A preferred range is 70°–120° C., for example 80° C. or 100° C., since these temperatures yield the best results in terms of efficiency to aldehydes and selectivity to n-aldehydes, coupled with an acceptable rate of reaction.

The total $(H_2+CO)$ initial pressure should be within the broad range 300–10000 kPa, depending on the precious metal used. For rhodium catalyst, the range is 300–3000 kPa, more preferred ranges being 500–2500 kPa and 800–1700 kPa. The $H_2$:CO ratio should preferably be 1:1 although ratios of up to about 5:1 may be selected if desired. Complete absence of hydrogen is undesirable.

We have found that under the various conditions discussed above we can achieve a high conversion of olefin with a high efficiency to aldehydes, the selectivity to n-aldehydes also being usefully high, the precious metal being readily recoverable from the aqueous phase. In particular, the experimental data for the hydroformylation of hex-1-ene and hexadec-1-ene in the presence and absence of amphiphilic reagent illustrates three important roles that the amphiphilic reagent plays:

(a) Rate—In the absence of amphiphilic reagent the rate of hydroformylation is lower by an order of magnitude. The amphiphilic reagent therefore provides a mechanism by which the reaction is rendered more favourable, for example by transferring the olefin to the aqueous phase.

(b) Selectivity—The presence of amphiphilic reagent increases the selectivity to the n-aldehyde.

(c) Efficiency—The presence of amphiphilic reagent increases the efficiency to the aldehyde.

Embodiments of the invention will now be described with reference to the following Examples and FIGURE which illustrates graphically the results of Examples 15 to 21.

(A) PREPARATION OF WATER-SOLUBLE PHOSPHINES 1. 4-Ph$_2$PC$_6$H$_4$CO$_2$H was prepared according to the method of Schiemenz (G Schiemenz, Chem. Ber., 1966,99,504).

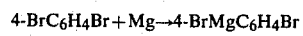

4-BrC$_6$H$_4$Br + Mg → 4-BrMgC$_6$H$_4$Br

Ph$_2$PCl + 4-BrMgC$_6$H$_4$Br → 4Ph$_2$P—C$_6$H$_4$Br

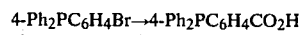

4-Ph$_2$PC$_6$H$_4$Br → 4-Ph$_2$PC$_6$H$_4$CO$_2$H 2. 3-Ph$_2$PC$_6$H$_4$SO$_3$Na was prepared according to the method of Ahrland and Chatt (S. Ahrland and V Chatt, J Chem. Soc., 1958,276).

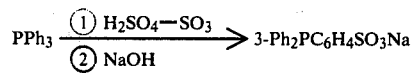

(B) PROCESS EXAMPLES

Example 1 to 10 show the general effectiveness of the use of an amphiphilic reagent according to the invention.

Example 1 (Comparative example)

A mixture of acetylacetonate-dicarbonyl rhodium (I) (0.015 g) and PPh$_2$(C$_6$H$_4$CO$_2$H) (0.177 g) was placed together with 20 mls of pH 10 buffer (NaHCO$_3$-NaOH), hex-1-ene (5 g) and heptane (5 g) in a glass pressure vessel which was flushed with nitrogen and pressurised to 560 kPa at 80° C. with magnetic stirring. The reactor was left at this pressure for 3 h. GC analysis of the organic layer indicated that there had been a 2.4% conversion of hex-1-ene to heptaldehydes and that the ratio of n-heptaldehyde to i-heptaldehyde was 20:1.

Example 2

The same procedure was adopted as in Example 1 except that lauryltrimethylammonium bromide (0.355 g) was added to the reaction mixture. Analysis of the organic phase after 1 hour indicated that 28% of the hex-1-ene had been converted to products. 98% of the products were present as heptaldehydes and the by products were internal olefins. The ratio of n-heptaldehyde to i-heptaldehyde was 87 to 1.

Example 3 (Comparative example)

The same procedure was adopted as in Example 1, except that hexadec-1-ene was used instead of hex-1-ene. Analysis of the organic phase after 3 hours indicated that 0.5% of the hexadec-1-ene had been converted to heptadecaldehydes.

Example 4

The same procedure was adopted as in Example 3 except that lauryl trimethylammonium bromide (0.355 g) was added to the reaction mixture. Analysis after 1 hour indicated that 73% of the hexadec-1-ene had been converted to products of which 89% was heptadecylaldehydes (n-heptadecyladehyde and i-heptadecylaldehyde). The ratio of n-heptadecylaldehyde to i-heptadecylaldehyde was 22:1.

Example 5 (Comparative example)

The same procedure was adopted as in Example 1 except that dodec-1-ene was used instead of hex-1-ene. Analysis after 3 hours indicated that 2.2% of the dodec-1-ene had been converted to tridecanals and that the ratio of n-tridecanal to i-tridecanal was 6:1.

Example 6

The same procedure was adopted as in Example 5 except that cetyltrimethylammonium bromide (0.422 g) was added to the reaction mixture. Analysis of the organic phase after 1 hour indicated that 78% of dodec-1-ene had been converted to products with an efficiency of 91% to tridecanals. The ratio of n-tridecanal to i-tridecanal was 20 to 1.

Example 7

The same procedure was adopted as in Example 5 except that lauryl trimethylammonium bromide (0.355 g) was added to the reaction mixture. Analysis of the organic phase after 1 hour indicated that 64% of the dodec-1-ene had been converted to products with an efficiency of 94% to tridecanals. The ratio of n-tridecanal to i-tridecanal was 16 to 1.

Example 8 (Comparative example)

The same procedure was adopted as in Example 5 except that neat dodec-1-ene (10 g) was used as the organic phase. Analysis of the organic phase after 3 hours indicated that 2.2% of the dodec-1-ene had been converted to tridecanals and that the ratio of n-tridecanal to i-tridecanal was 7:1.

Example 9

The same procedure was adopted as in Example 6 except that neat dodec-1-ene (10 g) was used as the organic phase. Analysis of the organic phase after 1 hour indicated that 44% of the dodec-1-ene had been converted to products with an efficiency of 85% to tridecanals. The ratio of n-tridecanal to i-tridecanal was 73 to 1.

Example 10

The same procedure was adopted as in Example 7 except that neat dodec-1-ene (10 g) was used as the organic phase. Analysis of the organic phase after 1 hour indicated that 43% of the dodec-1-ene had been converted to products with an efficiency of 82% to tridecanals and the ratio of n-tridecanal to i-tridecanal was 70 to 1.

The above Examples demonstrate the dramatic improvement in rate, conversion of olefin, efficiency to aldehydes and selectivity to n-aldehydes obtained from the use of an amphiphilic reagent.

Examples 11–14 indicate that a range of rhodium complexes can be used as catalyst precursors with similar activities, selectivities and efficiencies and with low rhodium loss to the organic phase. Results are given in Table 1 below. Conditions were as in Example 9.

TABLE 1

| | Hydroformylation of dodec-1-ene | | | |
|---|---|---|---|---|
| Example | Rhodium Precursor | Conversion % | Selectivity to n-tridecanal (n/i) | Efficiency to aldehydes % | [Rh] org ppm |
| 11 | [Rh(acac)(CO)$_2$] | 67 | 22 | 91 | 0.3 |
| 12 | [RhCl$_3$.3H$_2$O] | 86 | 27 | 87 | 0.3 |
| 13 | [Rh$_2$Cl$_2$($\eta^4$C$_8$H$_{12}$)$_2$] | 89 | 29 | 83 | 0.3 |
| 14 | [Rh($\eta^4$-C$_8$H$_{12}$)$_2$]BF$_4$ | 78 | 26 | 88 | 1.8 |

[Rh]$_{aq}$ = 300 ppm

Examples 15–21 illustrate that the hydroformylation of dodec-1-ene can be carried out at a range of rhodium concentrations. Results are quoted graphically in FIG. 1, in which the rate is quoted as the time taken for the pressure to drop from 560 to 520 kPa after the fifth successive pressurisation to 560 kPa.

Examples 22–35 illustrate that the hydroformylation may be performed with a range of $C_3$–$C_{20}$ olefins under mild conditions. Results appear in Table 2 below. Conditions were as in Example 1.

room temperature. Analysis of the organic phase indicated that 96% of the dodec-1-ene had been consumed and that 83% of the product was present as n- or i-tridecanal. The ratio of n to i tridecanal was 26:1. Rhodium was detected in the organic phase at levels of 5 ppm.

Examples 43–51 indicate that the reaction proceeds under a range of temperatures. Results are given in Table 4 below. Conditions were as in Example 36.

TABLE 2

Examples 22–35

| Example | Substrate | Amphiphilic reagent (A) | A:P:Rh | % Conversion | Selectivity n/i | Efficiency % |
|---|---|---|---|---|---|---|
| 22 | PROPYLENE | C7AB | 20:10:1 | — | 13 | — |
| 23 | HEX-1-ENE | CTAB | 5:3:1 | 51 | 11 | 89 |
| 24 | HEX-1-ENE | CTAB | 20:10:1 | 95 | 45 | 98 |
| 25 | HEX-1-ENE + heptane | CTAB | 20:10:1 | 52 | 34 | 100 |
| 26 | HEX-1-ENE + heptane | LTAB | 20:10:1 | 28 | 87 | 98 |
| 27 | HEXADEC-1-ENE | CTAB | 5:3:1 | 18 | 8 | 95 |
| 28 | OCT-1-ENE + heptane | CTAB | 20:10:1 | 33 | 57 | 92 |
| 29 | NON-1-ENE | CTAB | 20:10:1 | 51 | 50 | 91 |
| 30 | NON-1-ENE + heptane | LTAB | 20:10:1 | 50 | 81 | 80 |
| 31 | DEC-1-ENE | LTAB | 20:10:1 | 33 | 38 | 89 |
| 32 | TRIDEC-1-ENE | CTAB | 20:10:1 | 38 | 43 | 70 |
| 33 | TETRADEC-1-ENE | CTAB | 20:10:1 | 30 | 40 | 73 |
| 34 | OCTADEC-1-ENE + heptane | LTAB | 20:10:1 | 54 | 19 | 100 |
| 35 | E:CPS-1-ENE + heptane | LTAB | 20:10:1 | 64 | 25 | 95 |

Examples 36–41 indicate that the reaction can be carried out under a range of pressures with low Rh losses, good rates and good selectivities. Results are quoted in Table 3 below.

TABLE 3

Hydroformylation of dodec-1-ene: The effect of pressure variation

| Example | Pressure kPa | Rate ΔP (min) | Selectivity n:i aldehydes | Efficiency % | [Rh] in organic layer ppm |
|---|---|---|---|---|---|
| 36 | 544–510 | 2 | 4.7 | 78.5 | 2.29 |
| 37 | 884–850 | 1.25 | 8.4 | 91.3 | 2.0 |
| 38 | 1360–1326 | 0.7 | 7.8 | 90.0 | — |
| 39 | 1701–1667 | 0.5 | 5.5 | 92.4 | 5.0 |
| 40 | 2041–2006 | 0.3 | 7 | 90.0 | — |
| 41 | 2448–2414 | 3 | 3.6 | 85.6 | 3.6 |

80°, under 1:1 $H_2$/CO, CTAB:P:Rh = 20:10:1, [Rh] = 300 ppm organic:aqueous = 1:2, organic = 40 g dodec-1-ene

TABLE 4

Hydroformylation of dodec-1-ene - Temperature Variation

| Example | Temperature | Selectivity to n-tridecanal (n/i) | Efficiency to tridecanals |
|---|---|---|---|
| 43 | 20° | 5 | 100 |
| 44 | 40° | 5 | 98 |
| 45 | 60° | 5 | 97 |
| 46 | 80° | 6 | 92 |
| 47 | 100° | 5 | 87 |
| 48 | 110° | 3 | 64 |
| 49 | 120° | 4 | 73 |
| 50 | 130° | 3 | 66 |
| 51 | 160° | NO REACTION | |

Examples 52–56 indicate that the reaction proceeds under a variety of aqueous:organic phase ratios. Results are given in Table 5 below. Conditions were as in Example 9.

TABLE 5

Hydroformylation of dodec-1-ene

| Example | Volume of aqueous layer (ml) | Wt of dodec-1-ene (g) | Wt heptane (g) | Conversion % | Selectivity to n-tridecanals | Efficiency to tridecanals | [Rh] org ppm |
|---|---|---|---|---|---|---|---|
| 52 | 20 | 5 | 5 | 78 | 23 | 92 | 0.9 |
| 53 | 20 | 10 | 10 | 48 | 25 | 78 | 0.2 |
| 54 | 20 | 20 | 20 | 19 | 3.4 | 87 | 0.5 |
| 55 | 20 | 30 | 30 | No reaction | — | — | — |
| 56 | 7 | 10 | 10 | 13 | 3 | 80 | 0.3 |

Example 42—showing a $H_2$:CO ratio of 5:1

A glass reactor was charged with a mixture of Rhacac(CO)$_2$ (0.015 g), 4,Ph$_2$PC$_6$H$_4$COOH (0.0709 g), cetyl trimethylammonium bromide (0.106 g) with a pH 7 buffer (20 ml), hexane (10 g) and dodec-1-ene (10 g). The reactor was flushed with nitrogen and pressurised to 700 kPa hydrogen-carbon monoxide (5:1) at 80° C. with stirring. The reactor was periodically pressurised to 700 kPa with hydrogen-carbon monoxide (1:1) over 4 h. After this period the reactor was cooled down to Examples 57 to 76 illustrate the effect of various amphiphilic reagents. All reagents gave an improvement in rate, conversion, efficiency, selectivity and/or retention of rhodium in the aqueous phase, although some reagents are preferred over other in terms of overall activity. Examples 58 and 60, although having a rate of greater than 60 mins, were nevertheless proceeding faster than the corresponding reaction in the absence of amphiphilic reagent (for which see Example 8).

In Table 6, which gives the results of Examples 57 to 76, a rough indication of the amount of rhodium in the respective phases is given by the colour of the phase.

TABLE 6
Hydroformylation of dodec-1-ene

| Example | Amphiphilic reagent (A) | A:P:Rh | Conversion % | Selectivity to n-tridecanal n/i | Efficiency to aldehydes % | Rate (min) ΔP(5)560–520 kPA |
|---|---|---|---|---|---|---|
| 57 | *18-crown-6 | 5:3:1 | 40 | 3 | 88 | 9 |
| 58 | PhCH$_2$N$^+$Bu$_3$$^n$Cl$^-$ | 5:3:1 | 3 | 7 | 76 | >60 |
| 59 | Bu$_4$$^n$N$^+$Cl$^-$ | 5:3:1 | 77 | 6 | 73 | 30 |
| 60 | Bu$_4$$^n$N$^+$OH$^-$ | 5:3:1 | 3 | 6 | 90 | >60 |
| 61 | C$_{16}$H$_{33}$PBu$_3$$^n$Br$^-$ | 5:3:1 | 62 | 6 | 64 | 7 |
| 62 | Aliquat 336 [C$_{10}$H$_{21}$)$_3$NMeBr$^-$] | 5:3:1 | 76 | 2 | 78 | 3 |
| 63 | Benzethonium chloride | 5:3:1 | 28 | 5 | 82 | 16 |
| 64 | Tween 41 | 5:3:1 | 41 | 4 | 72 | 5 |
| 65 | Span 40 | 5:3:1 | 30 | 5 | 80 | 7 |
| 66 | Sodium dodecyl sulphate | 5:3:1 | 46 | 4 | 80 | 8 |
| 67 | Brij 35 | 5:3:1 | 32 | 14 | 87 | 18 |
| 68 | CTAB | 5:3:1 | 85 | 12 | 75 | 12 |
| 69 | CTAB | 20:10:1 | 36 | 115 | 76 | 7 |
| 70 | C$_{12}$H$_{25}$$\overset{+}{\text{N}}$Me$_3$Br$^-$ | 20:10:1 | 38 | 76 | 69 | 9 |
| 71 | **C$_{12}$H$_{25}$$\overset{+}{\text{N}}$Me$_3$Br$^-$ | 20:10:1 | 73 | 28 | 80 | 19 |
| 72 | C$_{14}$H$_{29}$$\overset{+}{\text{N}}$Me$_3$Br$^-$ | 20:10:1 | 34 | 70 | 78 | 9 |
| 73 | **C$_{14}$H$_{29}$$\overset{+}{\text{N}}$Me$_3$Br$^-$ | 20:10:1 | 63 | 13 | 84 | 18 |
| 74 | C$_{16}$H$_{33}$$\overset{+}{\text{N}}$C$_5$H$_5$Br$^-$ | 20:10:1 | 34 | 60 | 70 | 8 |
| 75 | C$_{16}$H$_{33}$$\overset{+}{\text{N}}$C$_5$H$_5$Br$^-$ | 20:10:1 | 83 | 20 | 81 | 5 |
| 76 | C$_{16}$H$_{33}$$\overset{+}{\text{N}}$Me$_3$CH$_3$CO$_2$$^-$ | 20:10:1 | 53 | 71 | 73 | 8 |

*In pH 10 KHCO$_3$ + KOH buffer
**Substrate: dodec-1-ene (5 g) + heptane (5 g)
All runs at 80°, 560–520 kPa 1:1 H$_2$/CO, organic: aqueous = 1:2, organic = dodec-1-ene (10 g) unless otherwise stated. Aqueous = pH 10 NaHCO$_3$ buffer.
Benzethonium chloride has the formula

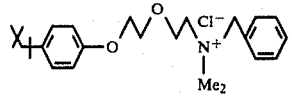

TABLE 6 (Cont)
Hydroformylation of dodec-1-ene

| Example | Colour of org. phase (ppm Rh) | Colour of aq. phase |
|---|---|---|
| 57 | yellow | yellow |
| 58 | yellow | brown |
| 59 | yellow | brown |
| 60 | yellow | brown |
| 61 | deep purple | colourless |
| 62 | deep purple | colourless |
| 63 | yellow | colourless |
| 64 | yellow | colourless |
| 65 | yellow | colourless |
| 66 | yellow | brown |
| 67 | colourless | brown |
| 68 | colourless (ca. 1 ppm) | brown |
| 69 | Colourless (0.55) | yellow |
| 70 | colourless (0.28) | clear orange |
| 71 | colourless (0.82) | clear orange |
| 72 | colorless (0.18) | clear orange |
| 73 | colourless (0.92) | clear orange |
| 74 | pale yellow (0.64 | yellow |
| 75 | yellow (1.95) | yellow |
| 76 | colourless | yellow |

Examples 77–86 illustrate phosphine variation. Results are given in Table 7 below. It is seen that an excess of amphiphilic reagent over phosphine is required for reaction to occur.

TABLE 7

| Example | Phosphine (P) | Amphiphilic Reagent (A) | A:P:Rh | Conversion % | Selectivity to n-tridecanal (n/i) | Efficiency to aldehydes % |
|---|---|---|---|---|---|---|
| 77 | 3-Ph$_2$PC$_6$H$_4$SO$_3$Na | None | 0:3:1 | 56 | 2.5 | 89 |
| 78 | 3,Ph$_2$PC$_6$H$_4$SO$_3$Na | Brij 35 | 5:3:1 | 37 | 7 | 81 |
| 79 | 3-Ph$_2$PC$_6$H$_4$SO$_3$Na | CTAB | 5:3:1 | 37 | 4 | 86 |
| 80 | 3,Ph$_2$PC$_6$H$_4$SO$_3$Na | CTAB | 5:8:1 | No reaction | | |
| 81 | 3-Ph$_2$PC$_6$H$_4$SO$_3$Na | CTAB | 5:15:1 | No reaction | | |
| 82 | 4-Ph$_2$PC$_6$H$_4$CO$_2$H | CTAB | 5:2:1 | 38 | 5 | 84 |
| 83 | 4-Ph$_2$PC$_6$H$_4$CO$_2$H | CTAB | 5:3:1 | 39 | 8 | 67 |
| 84 | 4-Ph$_2$PC$_6$H$_4$CO$_2$H | CTAB | 20:10:1 | 45 | 49 | 85 |
|  | 4-Ph$_2$PC$_6$H$_4$CO$_2$H | CTAB | 20:12:1 | 67 | 18 | 86 |
| 85 | P(C$_6$H$_4$CO$_2$H)$_3$ | CTAB | 5:3:1 | 28 | 9 | 70 |
| 86 | P(C$_6$H$_4$CO$_2$H)$_3$ | CTAB | 20:10:1 | 48 | 18 | 70 |

At 560 kPa, hydrogen-carbon monoxide (1:1), 80°
[Rh] = 300 ppm, Vol. of aqueous = 20 ml (pH 10 buffer)
Vol. of organic = 10 ml (dodec-1-ene)

Examples 87–90: hydroformylation of internal olefins

Example 87

A Baskerville-Lindsay autoclave (500 ml) was charged with a mixture of pH 10 bicarbonate buffer (0.1 M, 80 ml), [Rh(acac)(CO$_2$)] (0.06 g), Ph$_2$PC$_6$H$_4$COOH (0.71 g), cetyltrimethylammonium bromide (1.69 trans-2-heptene (5 g) and cyclohexane (40 g). The reactor was flushed with nitrogen and heated at 80° C. under 4,400 kPa hydrogen-carbon monoxide for 2½ h. The mixture was allowed to cool down to room temperature and the reactor was vented to atmospheric pressure. Centrifugation of the mixture gave a yellow aqueous phase and a colourless organic phase. GLC analysis of the organic phase indicated that 5% of the trans-hept-2-ene had been converted to octanals.

Example 88

The reactor was charged with reactants as in Example 87 except that the organic phase was composed of methyl oleate (10 g) and heptane (30 g). The reactor was heated at 80° C. under 10 kPa hydrogen-carbon monoxide (1:1). After the reaction the phases were separated by centrifugation to give a colourless organic phase and a yellow aqueous phase. Analysis of the organic phase by $^1$H NMR indicated that 20% of the olefinic group had been converted to aldehydes.

Example 89

The same conditions were used as in Example 88 except that the organic phase consisted of methyl linoleate (10 g) and heptane (30 g). After the reaction the phases were separated by centrifugation to give a colourless organic layer and a yellow aqueous phase. Analysis of the organic phase by $^1$H NMR indicated that 20% of the olefinic groups had been converted to aldehydes.

Example 90

The same conditions were used as in Example 88 except that the organic phase consisted of trans dec-5-ene (9 g) and heptane (31 g). GC analysis of the organic phase after reaction indicated that 10% of trans dec-5-ene had been converted to 2 butylheptanal. No by-products were observed.

Examples 91–106: use of complexes of Pd, Pt, Ru

Results are given in Table 8 below.

TABLE 8
Hydroformylation of dodec-1-ene

| Example | Complex | Phosphine (P) | Amphiphilic Reagent (A) | A:P:Pt | Pressure $10^3$ kPa | Conversion % | Selectivity to n-tridecanal (n/i) |
|---|---|---|---|---|---|---|---|
| 91 a–e | [Pd$_2$(dba)$_3$] | Ph$_2$PC$_6$H$_4$CO$_2$H | — | 0:2:1 | 5 | 4.0 | 4 |
| 92 a–e | [Pd$_2$(dba)$_3$] | Ph$_2$PC$_6$H$_4$CO$_2$H | C$_{16}$H$_{33}$NMe$_3$Br$^-$ | 5:2:1 | 5 | 2 | 6 |
| 93 a–e | K$_2$[PdCl$_4$] | Ph$_2$PC$_6$H$_4$CO$_2$H | C$_{16}$H$_{33}$NMe$_3$Br | 5:2:1 | 5 | 2 | 7 |
| 94 | [PtCl$_2$(PPh$_3$)$_2$] | As ligand | — | 0:2:1 | 10 | 3.5 | 2 |
| 95 b,d,e,g | K$_2$[PtCl$_4$] | 4Ph$_2$PC$_6$H$_4$COOH | — | 0:2:1 | 10 | 0.4 | 2 |
| 96 b,d,e,g | K$_2$[PtCl$_4$] | 4Ph$_2$PC$_6$H$_4$COOH | C$_{16}$H$_{33}$NMe$_3$Br$^-$ | 20:2:1 | 10 | 0.4 | 5 |
| 97 b,d,g,h | K$_2$[PtCl$_4$] | 4Ph$_2$PC$_6$H$_4$COOH | C$_{12}$H$_{25}$NMe$_3$Br$^-$ | 20:2:1 | 10 | 3 | 3 |
| 98 b,d,g,i | [PtCl$_2$(Ph$_2$PC$_6$H$_4$SO$_3$Na$_2$)] | As ligand | — | 0:2:1 | 10 | 0.6 | 2 |
| 99 b,d,g,i | [PtCl$_2$Ph$_2$PC$_6$H$_4$SO$_3$Na$_2$)] | As ligand | C$_{12}$H$_{25}$NMe$_3$Br$^-$ | 20:2:1 | 10 | 0.6 | 4 |
| 100 b,d,j | [PtCl$_2$(Ph$_2$PC$_6$H$_4$SO$_3$Na)$_2$] | As ligand | C$_{16}$H$_{33}$NMe$_3$Br$^-$ | 20:2:1 | 10 | 0.2 | 5 |
| 101 b,d,i | [RuCl$_3$3H$_2$O] | 4-Ph$_2$PC$_6$H$_4$CO$_2$H | — | 0:2:1 | 10 | 90 | 3 |
| 102 b,d,i | [RuCl$_3$3H$_2$O] | 4-Ph$_2$PC$_6$H$_4$CO$_2$H | C$_{16}$H$_{33}$NMe$_3$Br$^-$ | 5:2:1 | 10 | 14 | 7 |
| 103 b,d,i | Na$_3$[RuCl$_6$] | 4-Ph$_2$PC$_6$H$_4$CO$_2$H | — | 0:2:1 | 10 | 8 | 4 |
| 104 b,d,i | Na$_3$[RuCl$_6$] | 4-Ph$_2$PC$_6$H$_4$CO$_2$H | C$_{16}$H$_{33}$NMe$_3$Br$^-$ | 10:2:1 | 10 | 9 | 5 |
| 105 b,d,i | [Ru$_2$Cl$_4$(p-cymene)$_2$] | 4-Ph$_2$PC$_6$H$_4$CO$_2$H | C$_{16}$H$_{33}$NMe$_3$Br$^-$ | 5:2:1 | 10 | 30 | 3 |
| 106 b,d,i | [Ru$_2$Cl$_4$(p-cymene)$_2$] | 4-Ph$_2$PC$_6$H$_4$CO$_2$H | C$_{16}$H$_{25}$SO$_3^-$Na$^+$ | 5:2:1 | 10 | 31 | 3 |

Notes to Examples 91–106, Table 8.
a dba = dibenzylidene acetone
b [PGM] = 300 ppm
c Cu:Pd = 1:1 (as Cu(OAc)$_2$)
d organic:aqueous = 1:2 total volume = 120 ml
e In pH 4 buffer
f In toluene-methanol (3:2) total volume = 120 ml
g With added SnCl$_2$ (Sn:Pt = 5:1)
h In pH 7 buffer
i In pH 10 buffer
j = In water

What is claimed is:

1. A catalytic process for the hydroformylation of olefins having from 3 to 20 carbon atoms to produce a high n:iso ratio of aldehyde product comprising reacting together at elevated temperature and pressure the olefin, hydrogen and carbon monoxide in the presence of a catalyst comprising a water-soluble complex of a platinum group metal in a reaction medium comprising an aqueous phase and an organic phase and in the further presence of an amphiphilic reagent, the aqueous phase containing the catalyst, the organic phase containing the olefin, the amphiphilic reagent permitting the olefin to cross from the organic phase into the aqueous phase and enabling the resulting product aldehyde to cross into the organic phase, said amphiphilic reagent being substantially soluble in the aqueous phase and substantially insoluble in the organic phase, the reaction temperature being in the range 40°–150° C. and the reaction pressure being in the range 300–10000 kPa, the ratio of aqueous phase to organic phase being in the range of 0.33:1 to 5:1 and the concentration of amphiphilic reagent to precious metal being up to 100:1 on a molar basis.

2. A process according to claim 1 in which the organic phase comprises a reactant olefin and a solvent.

3. A process according according to claim 1 or claim 2 in which the reactant olefin is a terminal olefin having a carbon chain length of C$_3$–C$_{20}$.

4. A process according to claim 1 in which the platinum group metal is selected from rhodium, platinum, ruthenium and palladium.

5. A process according to claim 1 in which the aqueous phase contains a water-soluble phosphine in complex combination with a platinum group metal catalyst precursor compound or complex.

6. A process according to claim 5 in which the water-soluble phosphine is a sulphonated or carboxylated triaryl phosphine having the formula

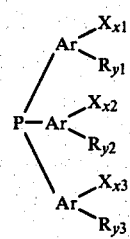

in which the Ar groups are the same or different aryl groups, the substituent R groups are the same or different and are selected from $C_1$-$C_4$ linear or branched chain alkyl or alkoxy groups, halogen, hydroxy, nitrile, nitro, amino and $C_1$-$C_4$ alkyl-substituted amino; the substituent X groups are the same or different and are selected from carboxylic acid, sulphonic acid and salt thereof; $x_1$, $x_2$ and $x_3$ are the same or different integers from 0-3 inclusive provided that at least $x_1$ is equal to or greater than 1; and $y_1$, $y_2$ and $y_3$ are the same or different integers from 0-5 inclusive.

7. A process according to claim 6 in which the water-soluble phosphine has the formula either

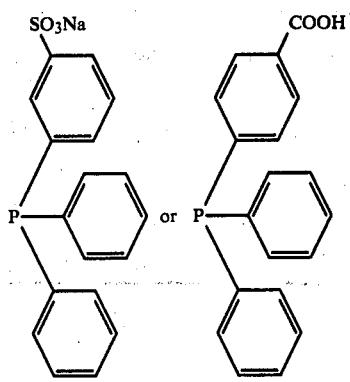

8. A process according to claim 7 in which the water-soluble phosphine is present in excess.

9. A process according to claim 1 in which the precious metal is present in a concentration in the range 100 to 500 ppm based on the aqueous phase.

10. A process according to claim 1 in which the amphiphilic reagent is selected from anionic, neutral, and cationic phase transfer reagents or surfactants.

11. A process according to claim 10 in which the cationic amphiphilic reagent is a complex ammonium salt.

12. A process according to claim 10 in which the neutral amphiphilic reagent is a polyoxyethylene.

13. A process according to claim 1 in which the precious metal is rhodium and the total initial pressure is within the range 300-3000 kPa.

14. A process according to claim 1 in which the $H_2$:CO ratio is within the range 1:1 to 5:1.

15. A process according to claim 1 in which the catalyst comprises a complex of a platinum group metal containing a water-soluble phosphine.

16. A process according to claim 15 in which the catalyst comprises a carbonyl complex of a platinum group metal.

17. A process according to claim 1 in which the catalyst comprises a hydrido-carbonyl complex of a platinum group metal.

* * * * *